United States Patent
Kim et al.

(10) Patent No.: US 6,320,045 B1
(45) Date of Patent: Nov. 20, 2001

(54) PROCESS FOR THE REDUCTION OF OXIRANYL EPOTHILONES TO OLEFINIC EPOTHILONES

(75) Inventors: Soong-Hoon Kim; James A. Johnson, both of Lawrenceville, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 09/316,796

(22) Filed: May 21, 1999

Related U.S. Application Data

(63) Continuation-in-part of application No. 09/170,581, filed on Oct. 13, 1998.
(60) Provisional application No. 60/082,563, filed on Apr. 21, 1998, and provisional application No. 60/067,549, filed on Dec. 4, 1997.

(51) Int. Cl.[7] ................................................. C07D 493/04
(52) U.S. Cl. ..................... 540/463; 548/204; 549/265; 549/266; 549/271
(58) Field of Search ........................... 540/463; 548/204; 549/265, 266, 271

(56) References Cited

FOREIGN PATENT DOCUMENTS

| | | |
|---|---|---|
| 4138042 | 5/1993 | (DE) . |
| 19542986 | 11/1995 | (DE) . |
| 19636343 | 8/1996 | (DE) . |
| 19639456 | 9/1996 | (DE) . |
| 19645361 | 10/1996 | (DE) . |
| 19645362 | 10/1996 | (DE) . |
| 19542986 | 5/1997 | (DE) . |
| 19639456 | 5/1997 | (DE) . |
| 19636343 | 3/1998 | (DE) . |
| 19645361 | 4/1998 | (DE) . |
| 19645362 | 4/1998 | (DE) . |
| 19647580 | 5/1998 | (DE) . |
| 19701758 | 7/1998 | (DE) . |
| 19707505 | 9/1998 | (DE) . |
| 19713970 | 10/1998 | (DE) . |
| 19720312 | 11/1998 | (DE) . |
| 19821954 | 11/1998 | (DE) . |
| 19726627 | 12/1998 | (DE) . |
| 879 605 | 11/1998 | (EP) . |
| 879 605 A2 | 11/1998 | (EP) . |
| 93/10121 | 5/1993 | (WO) . |
| 97/19086 | 5/1997 | (WO) . |
| 98/08849 | 3/1998 | (WO) . |
| 98/22461 | 5/1998 | (WO) . |
| 98/24427 | 6/1998 | (WO) . |
| 98/25929 | 6/1998 | (WO) . |
| 98/38192 | 9/1998 | (WO) . |
| 98/47891 | 10/1998 | (WO) . |
| 99/01124 | 1/1999 | (WO) . |
| 99/03848 | 1/1999 | (WO) . |
| 99/07692 | 2/1999 | (WO) . |

OTHER PUBLICATIONS

Balog, A., et al., "Total Synthesis of (−)-Epothilone A", *Angew. Chem., Int. Ed. Engl.* 35, 2801–2803 (1996).

Bertini, F., et al., "Alkenes from Epoxides by Reductive Elimination with Magnesium Bromide–Magnesium Amalgam", *Chem. Commun.* 1970, 144.

Bollag, D.M., et al., "Epothilones, A New Class of Microtubule–stabilizing Agents with a Taxol–like Mechanism of Action", *Cancer Res.* 55, 2325–2333 (1995).

Fujisawa, T., et al., "Deoxygenation of Epoxides to Olefins with $FeCl_3$—n–BuLi System", *Chem. Lett.*, 1974, 883–885.

(List continued on next page.)

*Primary Examiner*—Bruck Kifle
(74) *Attorney, Agent, or Firm*—Rena Patel; Joan E. Switzer

(57) ABSTRACT

The invention as claimed is directed to a process for making an epothilone having the following structures

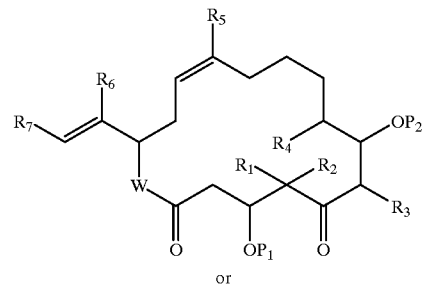

II or

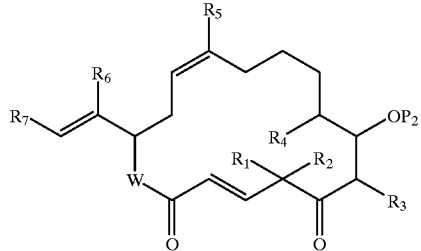

IV from ones having an oxiranyl moiety, by reacting a compound having the latter structure with a metal or metal-assisted reagent. Said metal or metal-assisted reagent is selected from the group consisting of a) reactive metallocenes; b) $[N_2C(CO_2Me)_2, cat\ Rh_2(OAC)_4]$; c) $[N_2C(CO_2Me)_2, cat[(n-C_7H_{15}CO_2)_2\ Rh]_2]$; d) [Zn—Cu, EtOH]; e) [Mg(Hg), MgBr]; f) Cr; g) $[FeCl_3, n-BuLi]$; h) $[TiCl_3, LiAlH_4]$; i) $[TiCl_4, Zn]$; j) $[WCl_6, LiAlH_4]$; k) $[NbCl_5, NaAlH_4]$; l) $[VCl_3, Zn]$ and m) $[WCl_6, n-BuLi]$.

4 Claims, No Drawings

OTHER PUBLICATIONS

Fujiwara, Y., et al., "Reductive Coupling of Carbonyl Compounds to Olefins by Tungsten Hexachloride–Lithium Aluminum Hydride and Some Tungsten and Molybdenum Carbonyls", *J. Org. Chem.*, vol. 43, No. 12, 1978, 2477–2479.

Gladysz, J. A., et al., "Deoxygenation of Epoxides by Metal Atom Cocondensation", *J. Org. Chem.*, vol. 41, No. 22, 1976, 3647–3648.

Hofle, G., et al., "Epothilone A and B—Novel 16–Membered Macrolides with Cytotoxic Activity: Isolation, Crystal Structure, and Conformation in Solution", *Angew. Chem., Int. Ed. Engl.* 35, 1567–1569 (1996).

Hofle, G., et al., "N–Oxidation of Epothilone A–C and O–Acyl Rearrangement to C–19 and C–21—Substituted Epothilones", Angew. *Chem. Int. Ed.*, vol. 38, No. 13/14, 1971–1974 (1999).

Inokuchi, T., et al., "Opening of Epoxides to Olefins or Halohydrins with Vanadium(II)–Tetrahydrofuran or Vanadium(III)–Tetrahydrofuran Complexes", *Synlett*, No. 6, 510–512 (1992).

Kowalski. R. J., et al., "Activities of the Microtubule–stabilizing Agents Epothilones A and B with Purified Tubulin and in Cells Resistant to Paclitaxel (Taxol®)" *J. Biol. Chem.* 272, 2534–2541 (1997).

Kupchan, S. M., et al., "Reductive Elimination of Epoxides to Olefins with Zinc–Copper COuple", *J. Org. Chem.*, vol. 36, No. 9, 1971, 1187–1190.

Martin, M. G., et al., "Epoxides as Alkene Protecting Groups. A Mild and Efficient Deoxygenation", *Tetrahedron Letters*, vol. 25, NO. 3, 251–254, 1984.

McMurry, J. E., et al., "Reduction of Epoxides to Olefins with Low Valent Titanium", *J. Org. Chem.*, vol. 40, No. 17, 1975, 2555–2556.

McMurry, J. E., et al., "Some Deoxygenation Reactions with Low–Valent Titanium ($TiCl_3$/$LiAlH_4$)", *J. Org. Chem.*, vol. 43, No. 17, 1978, 3249–3254.

Meng, D., et al., "Remote Effects in Macrolide Formation through Ring–Forming Olefin Metathesis: An Application to the Synthesis of FUlly Active Epothilone Congeners", *J. AM. Chem. Soc.* 119, 2733–2734 (1997).

Nicolaou, K. C., et al., "Synthesis of epothilones A and B in solid and solution phase", *Nature.* 387, 268–272 (1997).

Nicolaou, K. C., et al., "Total Syntheses of Epothilones A and B via a Macrolactonization–Based Strategy", *J. Am. Chem. Soc.* 119 (34) 7974–7991 (1997).

Nicolaou, K. C., et al., "Synthesis of epothilones A and B in solid and solution phase" (Correction to *Nature* 387, 268–272 (1997)) *Nature.* 390, p. 100 (1997).

Nicolaou, K. C., "Total Synthesis of Epothilone A: The Macrolactonization Approach", et al., *Angew. Chem., Int. Ed. Engl.* 36, 525–527 (1997).

Nicolaou, K. C., et al., "Designed Epothilones: Combinatorial Synthesis, Tubulin Assembly Properties, and Cytotoxic Action against Taxol–Resistant Tumor Cells", *Angew. Chem.* (36) No. 19, 1997, 2097–2103.

Raucher, S., et al., "Total Synthesis of (+)–Dihydrocostunolide via Tandem Cope–Claisen Rearrangement", *J. Org. Chem.*, 1986, 51, 5503–5505.

Sato, M, et al., "Reduction of Organic Compounds with Low–Valent Niobium ($NbCl_5$/$NaAlH_4$)", *Chem. Letters*, 1982, pp. 157–160.

Schinzer, D., et al., "Total Synthesis of (–)–Epothilone A", *Angew. Chem., Int. Ed. Eng.* 36, 523–524 (1997).

Schobert, R., et al., "Reduction and Isomerization of Oxiranes and α–Diazoketones by Various Early Transition Metallocenes", *Synlett*, No. 8, 1990, 465–466.

Sharpless, K. B., et al., "Lower Valent Tungsten Halides. A New Class of Reagents for Deoxygenation of Organic Molecules", *J. Amer. Chem. Soc.*, 94:18, Sep. 6, 1972, 6538–6540.

Su, D.–S., et al., "Total Synthesis of (–)–Epothilone B: An extension of the Suzuki Coupling Method and Insights into Structure–Activity Relationships of the Epothilones", *Angew. Chem., Int. Ed. Engl.* 36, 757–759 (1997).

Yang, Z., et al., "Total Synthesis of Epothilone A: The Olefin Metathesis Approach", *Angew. Chem., Int. Ed. Engl.* 36, 166–168 (1997).

Nicolaou, K. C., et al., "An Approach to Epothilones Based on Olefin Metathesis", *Angew. Chem. Int. Ed. Engl.*, vol. 35, No. 20, 2399–2401 (1996).

Nicolaou, K. C., et al., "Total Synthesis of Epothilone A: The Macrolactonization Approach", *Angew. Chem. Int. Ed. Engl.*, vol. 36, No. 5, 525–527 (1997).

Nicolaou, K.C., et al., "The Olefin Metathesis Approach to Epothilone A and Its Analogues", *J. Am. Chem. Soc.*, vol. 119, No. 34, 7960–7973 (1997).

Su, D.–S., et al., "Structure–Activity Relationships of the Epothilones and the First In Vivo Comparison with Paclitaxel", *Angew. Chem. Int. Ed. Engl.*, vol. 36, No. 19, 2093–2096 (1997).

Victory, S. F., et al., "Relative Stereochemistry and Solution Conformation of the Novel Paclitaxel–Like Antimitotic Agent Epothilone A", Bioorg. Med. Chem. Letts., vol. 6, No. 7, 893–898 (1996).

Winkler, J. D., et al., "A Model For The Taxol (Paclitaxel)/ Epothilone Pharmacophore", *Bioorg. Med. Chem. Letts.*, vol. 6, No. 24, 2963–2966 (1996).

Bollag, D., et al., "Epothilone, A New Structural Class of Microtubule Stabilizer", Abstract, *Proc. Am. Assoc. Cancer Res.*, vol. 36, 86 Meet. 454 (1995).

Bollag, D., "Epothilones: Novel Microtubule–Stabilising Agents", *Expert Opin. Invest. Drugs*, vol. 6, No. 7, 867–873 (1997).

Bertinato, P., et al., "Studies Toward a Synthesis of Epothilone A: Stereocontrolled Assembly of the Acyl Region and Models for Macrocyclization", J. Org. Chem., vol. 61, No. 23, 8000–8001 (1996).

*Chemical & Engineering News*, "Epothilone Epiphany: Total Syntheses", vol. 74, No. 52, 24–26 (1996).

*Chemical & Engineering News*, "First Total Synthesis of Epothilone B", vol. 75, No. 13, 23 (1997).

*Chemical & Engineering News*, "Solid–Phase Epothilone Synthesis Used to Create Analog Library", vol. 75, No. 20, 33, (1997).

Claus, E., et al., "Synthesis of the C1–C9 Segment of Epothilons", *Tetrahedron Lett.*, vol. 38, No. 8, 1359–1362 (1997).

De Brabander, J., et al., "Towards a Synthesis of Epothilone A: Rapid Assembly of the C1–C6 and C7–C12 Fragments", *Synlett*, vol. 7, 824–826 (1997).

Gabriel, T. and Wessjohann, L., "The Chromium–Reformatsky Reaction: Asymmetric Synthesis of the Aldol Fragment of the Cytotoxic Epothilons from 3–(2–Bromoacyl)–2–Oxazolidinones", *Tetrahedron Lett.*, vol. 38, No. 8, 1363–1366 (1997).

Gerth, K., et al., "Epothilons A and B: Antifungal and Cytotoxic Compounds from *Sorangiusm cellulosum* (Myxobacteria) Production, Physico–chemical and Biological Properties", *J. Antibiotics*, vol. 49, No. 6, 560–563 (1996).

Marshall, A., "Total Synthesis of Epothilone", *Nature Biotechnology*, vol. 15, No. 3, 205 (1997).

Sharpless, K. B., et al., "Lower Valent Tungsten Halides. A New Class of Reagents for Deoxygenation of Organic Molecules", *J. Amer. Chem. Soc.*, vol. 94, No. 18, 6538–6540 (1972).

Meng, D., et al., "Studies Toward a Synthesis of Epothilone A: Use of Hydropyran Templates for the Management of Acyclic Stereochemical Relationships", *J. Org. Chem.*, vol. 61, No. 23, 7998–7999 (1996).

Meng, D., et al., "Total Syntheses of Epothilones A and B", *J. Am. Chem. Soc.*, vol. 119, No. 42, 10073–10092 (1997).

Mensching, S. and Kalesse, M., "Generation of Thiazoles by Column Dehydrogenation of Thiazolidines with $MnO_2$", *J. Prakt. Chem.*, vol. 339, No. 1, 96–97 (1997).

Mulzer, J. and Mantoulidis, A., "Synthesis of the C(1)–C(9) Segment of the Cytotoxic Macrolides Epothilon A and B", *Tetrahedron Lett.*, vol. 37, No. 51, 9179–9182 (1996).

Nicolaou, K., et al., "Chemistry, Biology and Medicine of Selected Tubulin Polymerizing Agents", *Pure Appl. Chem.*, vol. 71, No. 6, 989–997 (1999).

Nicolaou, K., et al., "Total Synthesis of Epothilone E and Related Side–chain Modified Analogues Via a Stille Coupling Based Strategy", *Bioorg. Med. Chem.*, vol. 7, No. 5, 665–697 (1999).

Schinzer, D., et al., "Studies Towards the Total Synthesis of Epothilones: Asymmetric Synthesis of the Key Fragments", *Chem. Eur. J.*, vol. 2, No. 22, 1477–1482 (1996).

Taylor, R. and Haley, J., "Towards the Synthesis of Epothilone A: Enantioselective Preparation of the Thiazole Sidechain and Macrocyclic Ring Closure", *Tetrahedron Lett.*, vol. 38, No. 12, 2061–2064 (1997).

Schinzer, D., et al., "Syntheses of (–)–Epothilone A", *Chem. Eur. J.*, vol. 5, No. 9, 2483–2491 (1999).

Schinzer, D., et al., "Syntheses of (–)–Epothilone B", *Chem. Eur. J.*, vol. 5, No. 9, 2492–2500 (1999).

Nicolaou, K. C., et al., "Synthesis and Biological Properties of C12, 13–Cyclopropylepothilone A and Related Epothilones", *Chemistry & Biology*, vol. 5, No. 7, 365–372 (1998).

PROCESS FOR THE REDUCTION OF OXIRANYL EPOTHILONES TO OLEFINIC EPOTHILONES

This is a continuation-in-part of application Ser. No. 09/170,581, filed Oct. 13, 1998, which claims the benefit of U.S. Provisional Application Serial Nos. 60/082,563, filed Apr. 21, 1998, and 60/067,549, filed Dec. 4, 1997; said U.S. patent applications are hereby incorporated by reference as if set forth at length.

FIELD OF THE INVENTION

The present invention relates to a process for the preparation of olefinic epothilones from oxiranyl epothilones.

BRIEF DESCRIPTION OF THE INVENTION

The present invention is directed to a process for preparing compounds of formulas II and IV.

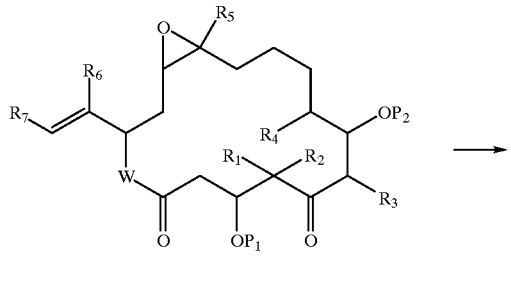

I

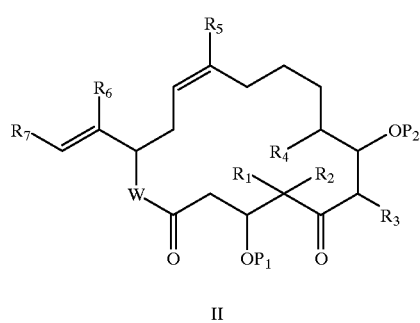

II

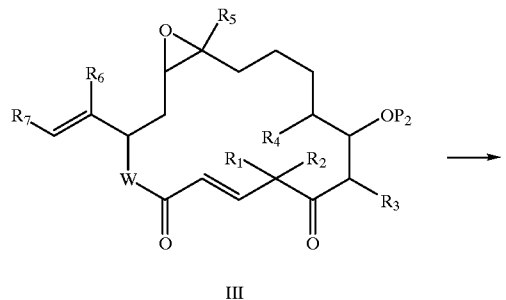

III

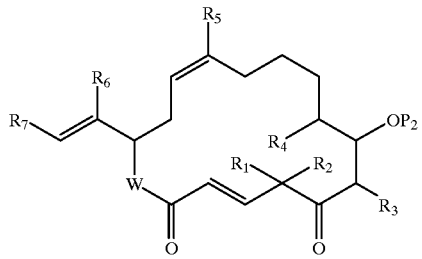

IV

The compounds of formulas I–IV are useful in the treatment of a variety of cancers and other abnormal proliferative diseases. Compounds of formula I are disclosed in Hofle et al., *Angew. Chem. Int. Ed. Engl.*, 1996, 35, No 13/14, 1567; WO93/10121 published May 27, 1993, and WO97/19086 published May 29, 1997, and also Nicolaou et al., *Angew Chem. Int. Ed. Engl.*, 1997, 36, No. 19, 2097 and Su et al., *Angew Chem. Int. Ed. Engl.*, 1997, 36, No. 19, 2093. Compounds of formula III are disclosed in Hofle et al., WO 97/19086 published May 29, 1997. As used in formulas II and IV, and throughout the specification, the symbols have the following meanings:

W is O or $NR_8$;

$R_1$, $R_2$, $R_3$, $R_4$, $R_5$, $R_6$, are selected from the group H, alkyl, substituted alkyl, or aryl and when $R_1$ and $R_2$ are alkyl can be joined to form a cycloalkyl;

$R_7$ is selected from the group consisting of H, alkyl, substituted alkyl, aryl, cycloalkyl, or heterocyclo;

$R_8$ is H, alkyl, or substituted alkyl, OH, O-alkyl, O-substituted alkyl;

$P_1$ and $P_2$ are selected from the group, H, alkyl, substituted alkyl, alkanoyl, substituted alkanoyl, aroyl, substituted aroyl, trialkylsilyl, aryl dialkylsilyl, diaryl alkylsilyl, triarylsilyl.

DETAILED DESCRIPTION OF THE INVENTION

Definitions:

Listed below are definitions of various terms used to describe this invention. These definitions apply to the terms as they are used throughout this specification, unless otherwise limited in specific instances, either individually or as part of a larger group.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, trifluoromethyl, trifluoromethoxy, hydroxy, alkoxy, cycloalkyoxy, heterocylooxy, oxo, alkanoyl, aryloxy, alkanoyloxy, amino, alkylamino, arylamino, aralkylamino, cycloalkylamino, heterocycloamino, disubstituted amines in which the 2 amino substituents are selected from alkyl, aryl or aralkyl, alkanoylamino, aroylamino, aralkanoylamino, substituted alkanoylamino, substituted arylamino, substituted aralkanoylamino, thiol, alkylthio, arylthio, aralkylthio, cycloalkylthio, heterocyclothio, alkylthiono, arylthiono, aralkylthiono, alkylsulfonyl, arylsulfonyl, aralkylsulfonyl, sulfonamido (e.g. $SO_2NH_2$), substituted sulfonamido, nitro, cyano, carboxy, carbamyl (e.g. $CONH_2$), substituted carbamyl (e.g. CONH alkyl, CONH aryl, CONH aralkyl or cases where there are two substituents on the nitrogen selected from alkyl, aryl or aralkyl), alkoxycarbonyl, aryl, substituted aryl, guanidino and heterocyclos, such as, indolyl, imidazolyl, furyl, thienyl, thiazolyl, pyrrolidyl, pyridyl, pyrimidyl and the like. Where noted above where the substituent is further substituted it will be with halogen, alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl group bonded directly through an alkyl group, such as benzyl.

The term "substituted aryl" refers to an aryl group substituted by, for example, one to four substituents such as alkyl; substituted alkyl, halo, trifluoromethoxy, trifluoromethyl, hydroxy, alkoxy, cycloalkyloxy, heterocyclooxy, alkanoyl, alkanoyloxy, amino, alkylamino, aralkylamino, cycloalkylamino, heterocycloamino, dialkylamino, alkanoylamino, thiol, alkylthio, cycloalkylthio, heterocyclothio, ureido, nitro, cyano, carboxy, carboxyalkyl, carbamyl, alkoxycarbonyl, alkylthiono, arylthiono, alkysulfonyl, sulfonamido, aryloxy and the like. The substituent may be further substituted by halo, hydroxy, alkyl, alkoxy, aryl, substituted aryl, substituted alkyl or aralkyl.

The term "cycloalkyl" refers to a optionally substituted, saturated cyclic hydrocarbon ring systems, preferably containing 1 to 3 rings and 3 to 7 carbons per ring which may be further fused with an unsaturated $C_3$–$C_7$ carbocyclic ring. Exemplary groups include cyclopropyl, cyclobutyl, cyclopentyl, cyclohexyl, cycloheptyl, cyclooctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, tetrahydrothiopyranyl, tetrahydrothiopyranyl sulfone, morpholinyl, thiomorpholinyl, thiomorpholinyl sulfoxide, thiomorpholinyl sulfone, 1,3-dioxolane and tetrahydro-1, 1-dioxothienyl, dioxanyl, isothiazolidinyl, thietanyl, thiiranyl, triazinyl, and triazolyl, and the like.

Exemplary bicyclic heterocyclic groups include benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl] or furo[2,3-b] pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl groups as described above or one or more groups described above as alkyl substituents. Also included are smaller heterocyclos, such as, epoxides and aziridines.

The term "alkanoyl" refers to —C(O)-alkyl.

The term "substituted alkanoyl" refers to —C(O)-substituted alkyl.

The term "aroyl" refers to —C(O)-aryl.

The term "substituted aroyl" refers to —C(O)-substituted aryl.

The term "trialkylsilyl" refers to —Si(alkyl)$_3$.

The term "aryl dialkylsilyl" refers to —Si(alkyl)$_2$(aryl).

The term "diaryl alkylsilyl" refers to —Si(aryl)$_2$(alkyl).

The term "heteroatoms" shall include oxygen, sulfur and nitrogen.

The term "metallocene" refers to an organometallic coordination compounds obtained as a cyclopentadienyl derivative of a transition metal or metal halide. For examples, see, *Hawley's Condensed Chemical Dictionary*, Twelfth Edition, Van Nostrand Reinhold Company, New York, 1993.

The term "metal-assisted reagent" refers to a reagent that is activated in the presence of a metal. For example, diazodimethyl malonate is activated in the presence of a rhodium catalyst, to give the corresponding reactive carbene.

Use and Utility:

The compounds of the invention are microtubule-stabilizing agents. They are thus useful in the treatment of a variety of cancers, including (but not limited to) the following;

carcinoma, including that of the bladder, breast, colon, kidney, liver, lung, ovary, pancreas, stomach, cervix, thyroid and skin; including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkins lymphoma, non-Hodgkins lymphoma, hairy cell lymphoma and Burketts lymphoma;

hematopoietic tumors of myeloid lineage, including acute and chronic myelogenous leukemias and promyelocytic leukemia;

other tumors, including melanoma, seminoma, tetratocarcinoma, neuroblastoma and glioma;

tumors of the central and peripheral nervous system, including astrocytoma, neuroblastoma, glioma, and schwannomas;

tumors of mesenchymal origin, including fibrosarcoma, rhabdomyoscaroma, and osteosarcoma; and other tumors, including melanoma, xenoderma pigmentosum, keratoactanthoma, seminoma, thyroid follicular cancer and teratocarcinoma.

Compounds of the invention may also inhibit tumor angiogenesis, thereby affecting the growth of tumors. Such anti-angiogenesis properties of the compounds of formulas II and IV may also be useful in the treatment of certain forms of blindness related to retinal vascularization, arthritis, especially inflammatory arthritis, multiple sclerosis, restinosis and psoriasis.

Compounds of the invention may induce or inhibit apoptosis, a physiological cell death process critical for normal development and homeostasis. Alterations of apoptotic pathways contribute to the pathogenesis of a variety of human diseases. Compounds of formula II and IV, as modulators of apoptosis, will be useful in the treatment of a variety of human diseases with aberrations in apoptosis including cancer (particularly, but not limited to follicular lymphomas, carcinomas with p53 mutations, hormone dependent tumors of the breast, prostrate and ovary, and precancerous lesions such as familial adenomatous polyposis), viral infections (including but not limited to herpesvirus, poxvirus, Epstein-Barr virus, Sindbis virus and adenovirus), autoimmune diseases (including, but not limited to, systemic lupus erythematosus, immune mediated glomerulonephritis, rheumatoid arthritis, psoriasis, inflammatory bowel diseases, and autoimmune diabetes mellitus), neurodegenerative disorders (including, but not limited to, Alzheimer's disease, AIDS-related dementia, Parkinson's disease, amyotrophic lateral sclerosis, retinitis pigmentosa, spinal muscular atrophy and cerebellar degeneration), AIDS, myelodysplastic syndromes, aplastic anemia, ischemic injury associated myocardial infarctions, stroke and reperfusion injury, arrhythmia, atherosclerosis, toxin-induced or alcohol induced liver diseases, hematological diseases (including, but not limited to, chronic anemia and plastic anemia), degenerative diseases of the musculoskeletal system (including, but not limited to, osteoporosis and arthritis), aspirin-sensitive rhinosinusitis, cystic fibrosis, multiple sclerosis, kidney diseases, and cancer pain.

The compounds of this invention are also useful in combination with known anti-cancer and cytotoxic agents and treatments, including radiation. If formulated as fixed dose, such combination products employ the compounds of this invention within the dosage range described below and the other pharmaceutically active agent within its approved dosage range. Compounds of formulas II and IV can be used sequentially with known anticancer or cytotoxic agents and treatment, including radiation when a combination formulation is inappropriate. Especially useful are cytotoxic drug combinations wherein the second drug chosen acts in a different phase of the cell cycle, e.g. S phase, than the present compounds of formulas II and IV which exert their effects at the $G_2$-M phase.

The compounds of the invention may exist as multiple optical, geometric and stereoisomers. While the process and schemes herein are depicted for one optical orientation, included within the present invention are all isomers and mixtures thereof.

The compounds of this invention can be formulated with a pharmaceutical vehicle or diluent for oral, intravenous or subcutaneous administration. The pharmaceutical composition can be formulated in a classical manner using solid or liquid vehicles, diluents and additives appropriate to the desired mode of administration. Orally, the compounds can be administered in the form of tablets, capsules, granules, powders and the like. The compounds are administered in a dosage range of about 0.05 to 200 mg/kg/day, preferably less than 100 mg/kg/day, in a single dose or in 2 to 4 divided doses.

Methods of Preparation:

Compounds of the invention can be prepared from compounds and by the methods described in the following schemes.

Compounds of formulas II and IV are prepared from compounds of formulas I and III, as shown in Scheme 1.

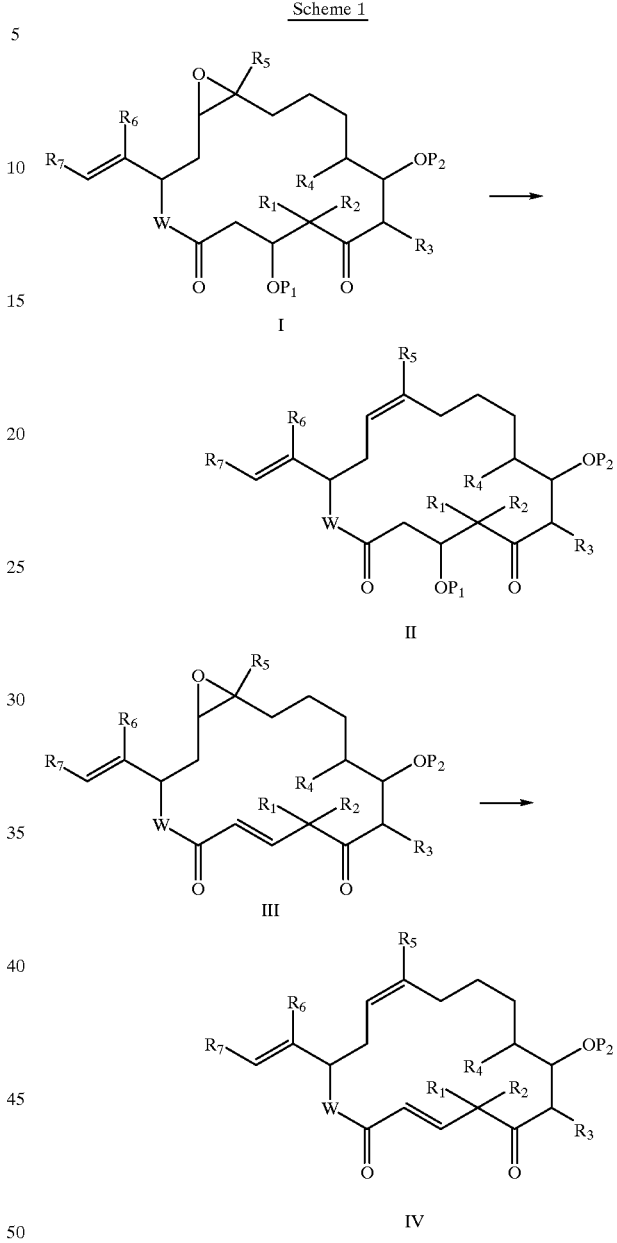

A compound of formula I or III affords compounds of formula II or, respectively, when treated with a reactive metallocene such as titanocene, zirconocene or niobocene (see, for example, R. Schobert and U. Hohlein, *Synlett*, 1990, No. 8, 465–466.). Optionally, compounds of formulas II or IV where $P_1$ and/or $P_2$ are hydroxyl protecting groups such as silanes, e.g., trialkylsilyl, and the like, can be deprotected by methods known in the art to provide compounds of formula II or IV where $P_1$ and $P_2$ are hydrogen. Other hydroxyl-protecting groups which are known in the art, and defined above as $P_1$ and $P_2$, can also be used (see, T. W. Greene and P. G. M. Wuts, *Protective Groups in Organic Synthesis*, John Wiley & Sons, Inc., New York, 1991).

Alternatively, other metal or metal-assisted reagents as listed below can be used for the conversion of a compound of formula I or III to a compound of formula II or IV. The protocols of these representative examples are incorporated herein as if set forth at length.

1) $N_2C(CO_2Me)_2$, cat $Rh_2(OAc)_4$:
Martin, M. G., Ganem, B., *Tett. Lett.*, 1984, 25, 251.
2) $N_2C(CO_2Me)_2$, cat $[(n-C_7H_{15}CO_2)_2Rh]_2$:
Rancher, S., Ki-Whan, C., Ki-Jun, H., Burks, J., *J. Org. Chem.*, 1986, 51, 5503.
3) Zn—Cu, EtOH:
Kupchen, S. M, Maruyama, M., *J. Org. Chem.*, 1971, 36, 1187.
4) Mg(Hg), $MgBr_2$:
Bertini, F., Grasselli, P., Zubiani, G., Cainelli, G., *Chem. Commun.*, 1970, 144.
5) Cr:
Gladysz, J. A., Fulcher, J. G., Togashi, S. *J. Org. Chem.*, 1976, 41, 3647.
6) $FeCl_3$, n-BuLi:
Fujisawa, T., Sugimoto, K., Ohta, H., *Chem. Lett,.* 1974, 883.
7) $TiCl_3$, $LiAlH_4$:
McMurry, J. E, Fleming, M. P., *J. Org. Chem.*, 1975, 40, 2555.
McMurry, J. E., Silvestri, M. G., Fleming, M. P., Hoz, T., Grayston, M. W., *J. Org. Chem.*, 1978, 43, 3249.
8) $TiCi_4$, Zn:
McMurry, J. E., Silvestri, M. G., Fleming, M. P., Hoz, T., Grayston, M. W., *J. Org. Chem.*, 1978, 43, 3249.
9) $WCl_6$, $LiAlH_4$:
Fugiwara, Y., Ishikawa, R., Akiyama, F., Teranishi, S., *J. Org. Chem.*, 1978, 43, 2477.
10) $NbCl_5$, $NaAlH_4$:
Sato, M, Oshima, K., *Chem. Lett.*, 1982, 157.
11) $VCl_3$, Zn:
Inokuchi, T., Kawafuchi, H., Torii, S., *Synlett*, 1992, 6, 510.
12) $WCl_6$, n-BuLi:
Sharpless, K. B., Umbret, M. A., Nieh, M. T., Flood, T. C., *J. Am. Chem. Soc.*, 1972, 94, 6538.

Preparation of the compounds of the present invention is illustrated in more detail by reference to the following non-limiting examples.

EXAMPLE 1

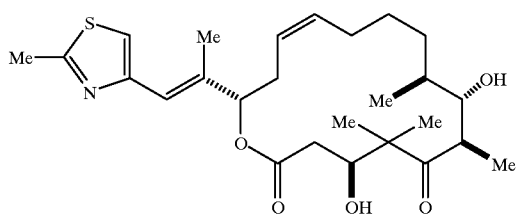

[4S-[4R*,7S*,8R*,9R*,15R*(E)]]-4,8-Dihydroxy-5,5,7,9-tetramethyl-16-[1-methyl-2-(2-methyl-4-thiazolyl)ethenyl]-1-oxa-13(Z)-cyclohexadecene-2,6-dione.
[Epothilone C]

To a two-necked flask was added chopped pieces of magnesium turnings (24 mg, 1.0 mmol). The flask was flame-dried under vacuum and cooled under argon. Bis(cyclopentadienyl)titanium dichloride (250 mg, 1.0 mmol) was added followed by anhydrous THF (5 mL). The stirring suspension was evacuated with low vacuum, and the reaction flask was refilled with argon. The red suspension became dark, turning a homogeneous deep green after 1.5 hours with nearly all the magnesium metal being consumed. An aliquot (3.5 mL, 0.70 mmol, 3.5 equivalents) was removed and cooled to −78° C. under argon. To this solution was added epothilone A (99 mg, 0.20 mmol, 1.0 equivalent). The reaction mixture was warmed to room temperature and stirred for 15 minutes. The volatiles were removed in vacuo and the residue was chromatographed two times on silica (25 g), eluting with 35% EtOAc/hexanes to give 76 mg (80%) of the title compound as a pale yellow viscous oil.

EXAMPLE 2

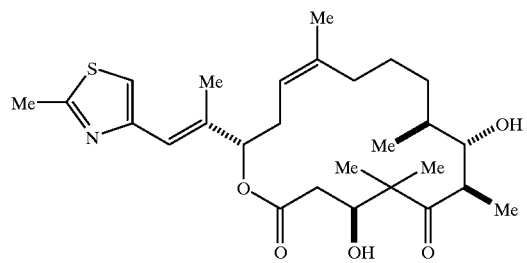

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-1-oxa-13(Z)-cyclohexadecene-2,6-dione.
[Epothilone D]

To anhydrous THF (5 ml) at −78° C. under argon was added $WCl_6$ (198 mg, 0.5 mmol) followed by nBuLi (0.625 ml of 1.6 M solution in hexanes, 1.0 mmol). The reaction was allowed to warm to room temperature over a 20 minute period. An aliquot (0.50 ml, 0.05 mmol) of the tungsten reagent was removed and added to epothilone B (9.0 mg, 0.018 mmol) under argon and the reaction mixture was stirred for 15 minutes, and then quenched by the addition of saturated $NaHCO_3$ (1 ml). The reaction mixture was extracted with EtOAc (3×1 ml), the combined extracts dried ($Na_2SO_4$), filtered, and the volatiles were removed under vacuum. The residue was chromatographed with 35% EtOAc/hexanes to give the title compound (7.0 mg, 0.014 mmol). MS m/z: 492.3 ($M^++H$).

EXAMPLE 3

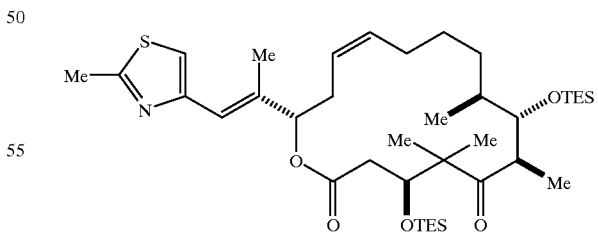

[4S-[4R*,7S*,8R*,9R*,15R*(E)]]-4,8-Triethylsilyloxy-5,5,7,9-tetramethyl-16-[1-methyl-2-(2-methyl-4-thiazolyl)ethenyl]-1-oxa-13(Z)-cyclohexadecene-2,6-dione.
[Bis-Triethylsilyl Epothilone C]

$Et_3SiCl$ (4.15 mmol, 0.700 ml) was added to epothilone A (0.415 mmol, 205 mg), imidazole (2.07 mmol, 140 mg) and i-Pr$_2$EtN (6.22 mmol, 1.08 ml) in DMF (5 ml). The resulting solution was heated at 40° C. After 16 hours, additional Et$_3$SiCl (2.07 mmol, 0.350 ml) and i-Pr$_2$EtN (4.15 mmol, 0.725 ml) were added and the resulting solution stirred at 60° C. for 48 hours. The reaction was concentrated, and the residue was purified with flash chromatography (10% EtoAc/Hexanes). Bis-triethylsilyl epothilone A was isolated as colorless oil (264 mg, 88%). MS (M$^+$+H) 722.

To anhydrous THF (5 ml) at −78° C. under argon was added WCl$_6$ (198 mg, 0.5 mmol) followed by nBuLi (0.625 ml of 1.6 M solution in hexanes, 1.0 mmol). The reaction was allowed to warm to room temperature over a 20 minute period. An aliquot (1.0 ml, 0.089 mmol) of the tungsten reagent was removed and added to bis-triethylsilyl epothilone A (22.5 mg, 0.031 mmol) under argon and the reaction stirred for 20 minutes then quenched by the addition of saturated NaHCO$_3$ (1 ml). The reaction mixture was extracted with EtOAc (3×1 ml), the combined extracts dried (Na$_2$SO$_4$), filtered, and the volatiles were removed under vacuum. The residue was chromatographed with 10% EtOAc/hexanes to give the title compound (13.6 mg, 0.019 mmol) in 62% yield. MS m/z: 706.5 (M$^+$+H).

EXAMPLE 4

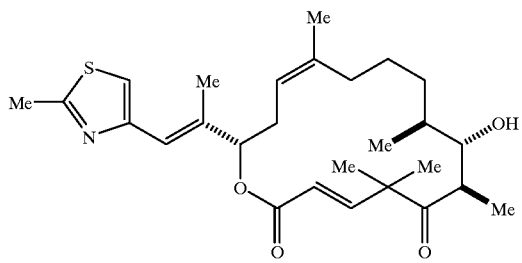

[7R-[7R*,8S*,9S*,15R*(E)]]-8-Hydroxy-5,5,7,9,13-pentamethyl-16-[1-methyl-2-(2-methyl-4-thiazolyl)ethenyl]-1-oxa-3(E),13(Z)-cyclohexadecadiene-2,6-dione.

The title compound was prepared following the procedure described in Example 2. From 10 mg of [1S-[1R*,3R*(E),10S*,11S*,12R*,16S*]]-11-hydroxy-8,8,10,12,-pentamethyl-3-[1-methyl-2-(2-methyl-4-thiazolyl)ethenyl]-4,17-dioxabicyclo [14.1.0]heptadec-6-ene-5,9-dione (prepared from epothilone B using the procedure described in WO97/19086 for the analogous conversion of epothilone A), 4.5 mg of title compound was obtained. MS 474 (M+H)$^+$.

EXAMPLE 5

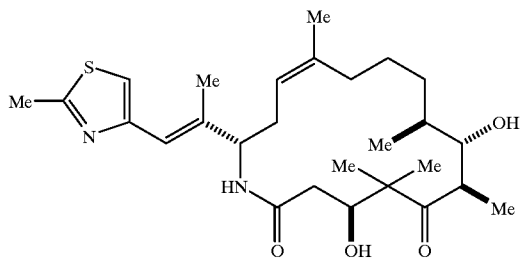

[4S-[4R*,7S*,8R*,9R*,15R*(E)]]-4,8-Dihydroxy-5,5,7,9,13-pentamethyl-16-[1-methyl-2-(2-methyl-4-thiazolyl)ethenyl]-1-aza-13(Z)-cyclohexadecene-2,6-dione A. (3S,6R,7S,8S,12R,13S,15S)-15-Azido-12,13-epoxy-4,4,6,8,12,16-hexamethyl-7-hydroxy-17-(2-methyl-4-thiazolyl)-5-oxo-16-heptadecenoic acid.

A solution of epothilone B (0.35 g, 0.69 mmol) in degassed THF (4.5 mL) was treated with a catalytic amount (80 mg, 69 mmol) of tetrakis(triphenylphosphine) palladium (0) and the suspension was stirred at 25° C., under argon for 30 minutes. The resulting bright yellow, homogeneous solution was treated all at once with a solution of sodium azide (54 mg, 0.83 mmol) in degassed H$_2$O (2.2 mL). The reaction mixture was warmed to 45° C. for 1 h, diluted with H$_2$O (5 mL) and extracted with EtOAc (4×7 mL). The organic extracts were washed with saturated aqueous NaCl (15 mL), dried (Na$_2$SO$_4$), and concentrated in vacuo. The residue was purified by flash chromatography (SiO$_2$, 3.0×15 cm, 95:5.0:0.5 CHCl$_3$-MeOH-AcOH) to afford Compound A (0.23 g, 61%) as a colorless oil. MS (ESI$^+$): 551 (M+H)$^+$; MS(ESI$^-$): 549 (M−H)$^-$.

B. (3S,6R,7S,8S,12R,13S,15S)-15-Amino-12,13-epoxy-4,4,6,8,12,16-hexamethyl-7-hydroxy-17-(2-methyl-4-thiazolyl)-5-oxo-16-heptadecenoic acid.

A solution of Compound A (0.23 g, 0.42 mmol) in THF (4.0 mL) was treated with H$_2$O (23 mL, 1.25 mmol) and polymer supported triphenylphosphine (Aldrich, polystyrene cross-linked with 2% DVB, 0.28 g, 0.84 mmol) at 25° C. The resulting suspension was stirred at 25° C. under argon (32 hours), filtered through a Celite pad and concentrated in vacuo. The residue was purified by flash chromatography (SiO$_2$, 1.5×10 cm, 95:5.0:0.5 to 90:10:1.0 CHCl$_3$-MeOH-AcOH gradient elution) to afford Compound B (96 mg, 44%) as a colorless oil. MS (ESI$^+$): 525.2 (M+H)$^+$; MS (ESI$^-$): 523.4 (M−H)$^-$.

Alternatively, to a 25 mL round-bottom flask charged with Compound A (0.26 g, 0.47 mmol) and PtO$_2$ (0.13 g, 50 wt %) was added absolute EtOH under argon. The resulting black mixture was stirred under one atmosphere of H$_2$ for 10 hours, after which time the system was purged with N$_2$ and an additional portion of PtO$_2$ (65 mg, 25 wt %) was added. Once again the reaction mixture was stirred under a blanket of H$_2$ for 10 hours. The system was then purged with N2, and the reaction mixture was filtered through a Celite pad eluting with CH$_2$Cl$_2$ (3×25 mL). The solvents were removed in vacuo and the residue was purified as described above to afford Compound B (0.19 g, 75%).

Alternatively, a solution of Compound A (20 mg, 36 mmol) in THF (0.4 mL) was treated with triphenylphosphine (19 mg, 73 mmol) under argon. The reaction mixture was warmed to 45° C., stirred for 14 hours and cooled to 25° C. The resulting iminophosphorane was treated with ammonium hydroxide (28%, 0.1 mL) and once again the reaction mixture was warmed to 45° C. After 4 hours, the volatiles were removed in vacuo and the residue was purified as described above to afford Compound B (13 mg, 70%).

C. [1S-[1R*,3R*(E),7R*,10S*,11S*,12R*,16S*]]-7,11-Dihydroxy-8,8,10,12,16-pentamethyl-3-[1-methyl-2-(2-methyl-4-thiazolyl)ethenyl]-4-aza-17-oxabicyclo[14.1.0]heptadecane-5,9-dione.

A solution of Compound B (0.33 g, 0.63 mmol) in degassed DMF (250 mL) was treated with solid NaHCO$_3$ (0.42 g, 5.0 mmol) and diphenylposphoryl azide (0.54 mL, 2.5 mmol) at 0° C. under argon. The resulting suspension was stirred at 4° C. for 24 hours, diluted with phosphate buffer (250 mL, pH=7) at 0° C. and extracted with EtOAc (5×100 mL). The organic extracts were washed with 10% aqueous LiCl (2×125 mL), dried ($Na_2SO_4$) and concentrated in vacuo. The residue was first purified by flash chromatography ($SiO_2$, 2.0×10 cm, 2–5% MeOH-$CHCl_3$ gradient elution) and then repurified using a Chromatotron (2 mm $SiO_2$, GF rotor, 2–5% MeOH-$CHCl_3$ gradient elution) to afford the title compound (0.13 g, 40%) as a colorless oil: $^1$H NMR ($CDCl_3$, 400 MHz) d 6.98 (s, 1 H), 6.71 (d, 1H, NH, J=8.1 Hz), 6.56 (s, 1 H), 4.69–4.62 (m, 1 H), 4.18–4.12 (m, 1 H), 4.01–3.96 (m, 1 H), 3.86 (s, 1 H), 3.38–3.34 (m, 1 H), 2.82 (dd, 1 H, J=5.6, 6.0 Hz), 2.71 (s, 3 H), 2.58 (s, 1 H), 2.43 (dd, 1 H J=9.0, 14.5 Hz), 3.34 (dd, 1 H, J=3.0, 14.5 Hz), 2.14 (s, 3 H), 2.05–1.92 (m, 2 H), 1.82–1.41 (a series of multiplets, 7 H), 1.35 (s, 3 H), 1.28 (s, 3 H), 1.18 (d, 3 H, J=6.8 Hz), 1.14 (s, 3 H), 1.00 (d, 3 H, J=6.8 Hz); MS (ESI$^+$): 507.2 (M+H)$^+$; MS(ESI$^-$): 505.4 (M–H)$^-$.

D. [4S-[4R*,7S*,8R*,9R*,15R*(E) ]]-4,8-Dihydroxy-5,5,7,9,13-pentamethyl-16-[1-methyl-2-(2-methyl-4-thiazolyl)ethenyl]-1-aza-13(Z)-cyclohexadecene-2,6-dione.

Tungsten hexachloride (0.19 g, 0.49 mmol, 0.5 equivalents) was dissolved in THF (5.0 ml) and the solution was cooled to –78° C. n-Butyllithium in hexane (1.6M, 0.63 ml, 1.0 mmol, 1.0 equiv) was added in one portion and the reaction mixture was allowed to warm to room temperature over 20 minutes (the solution turned dark green upon warming to room temperature). A 0.1M solution of the prepared tungsten reagent (0.79 ml, 0.079 mmol, 2.0 mmol) was added to Compound C (0.020 g, 0.039 mmol, 1.0 equivalent). The reaction mixture was stirred at room temperature for 30 minutes and then was quenched with saturated $NaHCO_3$ (2.0 ml). The quenched solution was diluted with water (10 ml) and the solution was extracted with $CH_2Cl_2$ (4×20 ml). The combined organic extracts were dried ($Na_2SO_4$), filtered and concentrated under vacuum. The inorganics were removed by passing the residue through a silica gel plug (eluting with 19/1 $CHCl_3$/MeOH). The eluent was concentrated under vacuum. The residue was purified by phplc (YMC-S5 ODS, 30–100% B, A=5% aqueous $CH_3CN$, B=95% aqueous $CH_3CN$, 3 ml/min, 220 nm, 30 minutes gradient) and the appropriate fractions were concentrated under vacuum. The sticky solid was lyophilized from aqueous acetonitrile to afford title compound (4.3 mg, 29%) as a white solid. TLC: Rf=0.57 (9/1 $CHCl_3$/MeOH, visualization by UV), HRMS: (M+H)+ calc=491.29436, found=491.2934.

What is claimed:

1. A process to produce a compound of the formulas

II

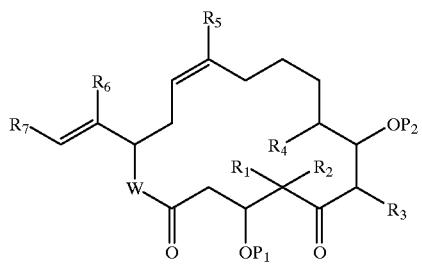

-continued
or

IV

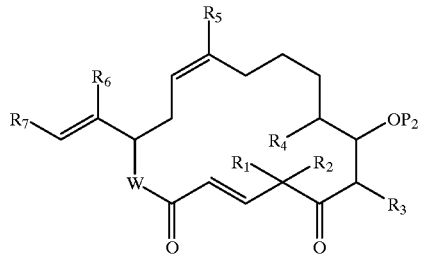

wherein

W is O or $NR_8$;

$R_1$, $R_2$, $R_3$, $R_4$, $R_5$, $R_6$, are selected from the group consisting of H, alkyl, substituted alkyl and aryl, and when $R_1$ and $R_2$ are alkyl can be joined to form a cycloalkyl;

$R_7$ is selected from the group consisting of H, alkyl, substituted alkyl, aryl, cycloalkyl and 4 to 7 membered ring systems having 1, 2, or 3 heteroatoms, wherein the heteroatoms are independently nitrogen, oxygen, or sulfur; and $R_8$ is selected from the group consisting of H, alkyl, substituted alkyl, OH, O-alkyl, and O-substituted alkyl; and $P_1$ and $P_2$ are selected from the group consisting of H, alkyl, substituted alkyl, alkanoyl, substituted alkanoyl, aroyl, substituted aroyl, trialkylsiyl, aryl dialkylsilyl, diaryl alkylsilyl, and triarylsilyl;

which comprises reacting a compound of the formula

I

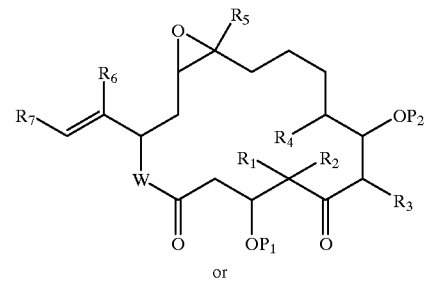

or

III

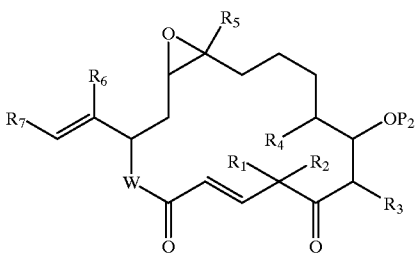

wherein

W, $R_1$, $R_2$, $R_3$, $R_4$, $R_5$, $R_6$, $R_7$, $R_8$, $P_1$ and $P_2$, are as above; with a metal or metal-assisted reagent, wherein said metal or metal-assisted reagent is selected from the group consisting of a) reactive metallocenes; b) {$N_2$C ($CO_2Me$)$_2$, cat $Rh_2$,(OAC)$_4$}; c) {$N_2$C($CO_2Me$)$_2$, cat{

(n-C$_7$H$_{15}$CO$_2$)$_2$Rh}$_2$}; d) {Zn—Cu, EtOH}; e) {Mg(Hg), MgBr}; f) Cr; g) {FeCl$_3$, n-BuLi}; h) {TiCl$_3$, LiAlH$_4$}; i) {TiCl$_4$, Zn}; j) {WCl$_6$, LiAlH$_4$,}; k) {NbCl$_5$, NaAlH$_4$}; l) {VCl$_3$, Zn}; and m) {WCl$_6$, n-BuLi}.

2. The process of claim 1 wherein the metal or metal-assisted reagent is a metallocene.

3. The process of claim 2 wherein the metallocene is selected from the group consisting of titanocene, zirconocene and niobocene.

4. The process of claim 1 wherein the metal or metal-assisted reagent is WCl$_6$, n-BuLi.

* * * * *